(12) United States Patent
Kharas et al.

(10) Patent No.: US 8,383,691 B2
(45) Date of Patent: Feb. 26, 2013

(54) METHODS OF MAKING IMPROVED COBALT-MOLYBDENUM-SULFIDE CATALYST COMPOSITIONS FOR HIGHER ALCOHOL SYNTHESIS

(75) Inventors: Karl Kharas, Louisville, CO (US); Jason P. Durand, Paramus, NJ (US); William A. May, Longmont, CO (US)

(73) Assignee: Albemarle Corporation, Baton Rouge, LA (US)

( * ) Notice: Subject to any disclaimer, the term of this patent is extended or adjusted under 35 U.S.C. 154(b) by 387 days.

(21) Appl. No.: 12/824,549

(22) Filed: Jun. 28, 2010

(65) Prior Publication Data
US 2010/0331581 A1 Dec. 30, 2010

Related U.S. Application Data

(60) Provisional application No. 61/221,796, filed on Jun. 30, 2009.

(51) Int. Cl.
*C07C 27/00* (2006.01)
*B01J 27/051* (2006.01)
(52) U.S. Cl. ...................... 518/714; 502/220
(58) Field of Classification Search ........................ None
See application file for complete search history.

(56) References Cited

U.S. PATENT DOCUMENTS

| | | | |
|---|---|---|---|
| 4,430,442 A | 2/1984 | Sawyer et al. | |
| 4,752,623 A | 6/1988 | Stevens | |
| 4,825,013 A | 4/1989 | Quarderer et al. | |
| 4,882,360 A | 11/1989 | Stevens | |
| 5,034,430 A | 7/1991 | Babler | |
| 6,617,464 B2 | 9/2003 | Manzer | |
| 6,635,599 B1 | 10/2003 | Eijsbouts et al. | |

OTHER PUBLICATIONS

C.H. Chang et al., "Infrared and Raman Studies of Amorphous MoS3 and Poorly Crystalline MoS2", J. Catal., vol. 72, pp. 139-148 (1981).
Pio Forzatti et al., "Higher Alcohol Synthesis", Catalysis Reviews, 33:1, 109-168 (Feb. 1, 1991).
S. Phillips et al., "Thermochemical Ethanol via Indirect Gasification and Mixed Alcohol Synthesis of Lignocellulosic Biomass", NREL Technical Report/TP-510-41168 (Apr. 2007).
I. Simakova et al., "Complex Mediums VI: Light and Complexity", edited by Martin W. McCall et al., Proceedings of SPIE, vol. 5924, 592413-1 through 592413-7, 2005.
H.W. Wang et al., "Synthesis of Molybdenum Disulphide by Acidification of Ammonium Tetrathiomolybdate Solutions", Journal of Materials Science Letters, vol. 15, No. 6, pp. 494-496 (Mar. 15, 1996).

*Primary Examiner* — Michael Barker
(74) *Attorney, Agent, or Firm* — Jeremy J. Kliebert; Marcy M. Hoefling; James A. Jubinsky

(57) ABSTRACT

This invention improves prior methods of making cobalt-molybdenum-sulfide catalysts for alcohol production from syngas. In one aspect, improved methods are provided for making preferred cobalt-molybdenum-sulfide compositions. In another aspect, processes utilizing these catalysts for producing at least one $C_1$-$C_4$ alcohol, such as ethanol, from syngas are described.

38 Claims, 4 Drawing Sheets

METHODS OF MAKING IMPROVED COBALT-MOLYBDENUM-SULFIDE CATALYST COMPOSITIONS FOR HIGHER ALCOHOL SYNTHESIS

PRIORITY DATA

This patent application claims priority under 35 U.S.C. §120 from U.S. Provisional Patent Application No. 61/221,796 for "METHODS OF MAKING IMPROVED COBALT-MOLYBDENUM-SULFIDE CATALYST COMPOSITIONS FOR HIGHER ALCOHOL SYNTHESIS," filed Jun. 30, 2009, the disclosure of which is hereby incorporated by reference herein for all purposes.

FIELD OF THE INVENTION

The present invention generally relates to the field of processes for the chemical conversion of synthesis gas to alcohols, such as ethanol. The invention relates to catalyst compositions, methods of making catalyst compositions, and methods of using catalyst compositions.

BACKGROUND OF THE INVENTION

Synthesis gas (hereinafter referred to as syngas) is a mixture of hydrogen ($H_2$) and carbon monoxide (CO). Syngas can be produced, in principle, from virtually any material containing carbon. Carbonaceous materials commonly include fossil resources such as natural gas, petroleum, coal, and lignite; and renewable resources such as lignocellulosic biomass and various carbon-rich waste materials. It is preferable to utilize a renewable resource to produce syngas because of the rising economic, environmental, and social costs associated with fossil resources.

There exist a variety of conversion technologies to turn these feedstocks into syngas. Conversion approaches can utilize a combination of one or more steps comprising gasification, pyrolysis, steam reforming, and/or partial oxidation of a carbon-containing feedstock.

Syngas is a platform intermediate in the chemical and biorefining industries and has a vast number of uses. Syngas can be converted into alkanes, olefins, oxygenates, and alcohols. These chemicals can be blended into, or used directly as, diesel fuel, gasoline, and other liquid fuels. Syngas can also be directly combusted to produce heat and power.

Since the 1920s it has been known that mixtures of methanol and other alcohols can be obtained by reacting syngas over certain catalysts (Forzatti et al., *Cat. Rev.-Sci. and Eng.* 33(1-2), 109-168, 1991). Fischer and Tropsch observed around the same time that hydrocarbon-synthesis catalysts produced linear alcohols as byproducts (Fischer and Tropsch, *Brennst.-Chem.* 7:97, 1926).

More recently, technology developers for these catalysts have included Dow Chemical/Union Carbide and Institut Francais du Petrole. Dow Chemical and Union Carbide jointly developed a sulfided mixed-alcohol catalyst based on molybdenum, $MoS_2$ (Phillips et al., National Renewable Energy Laboratory TP-510-41168, April 2007). U.S. Pat. No. 4,752,623 (Stevens and Conway), originally assigned to Dow Chemical, discloses a cobalt-molybdenum-sulfide catalyst for producing mixed alcohols from syngas.

To produce these cobalt-molybdenum-sulfide catalysts, according to U.S. Pat. No. 4,752,623 and other related patents, ammonium heptamolybdate is dissolved in water and heated to 60° C., and then ammonium sulfide is added to make $[NH_4]_2MoS_4$. In a separate container, cobalt acetate is dissolved. These two solutions are added simultaneously to a third vessel containing heated acetic acid. The catalyst precursor precipitates. The precipitate is filtered, dried in air, and calcined at 500° C. This chemistry can be difficult, with certain compounds undesirably precipitating out of solution.

In light of the shortcomings in the art, improved methods of making effective cobalt-molybdenum-sulfide catalysts are needed. These methods should identify important factors and conditions during the synthesis of preferred catalysts, so that a person of ordinary skill in the art can make and use these catalysts to commercially produce alcohols, such as ethanol, from syngas.

SUMMARY OF THE INVENTION

In some variations, the present invention provides a method for making a cobalt-molybdenum-sulfide composition, the method comprising the steps of:

(i) dissolving ammonium dimolybdate, $[NH_4]_2[Mo_2O_7]$, in aqueous ammonia, thereby producing a molybdate solution;

(ii) combining hydrogen sulfide with at least some of the molybdate solution, thereby producing a tetrathiomolybdate solution comprising $[MoS_4]^{2-}$;

(iii) combining a Co(II) solution with at least some of the tetrathiomolybdate solution to form a first precipitate within a suspension;

(iv) combining sulfuric acid with at least some of the suspension, to form a second precipitate;

(v) filtering the second precipitate, wherein the filtering removes a portion of water present in the second precipitate, thereby creating a filter cake;

(vi) thermally processing the filter cake to produce a calcined material comprising cobalt, molybdenum, and sulfur.

Step (i) can be conducted at a temperature selected from about 10-80° C., for example. In some embodiments, in step (i), the ratio of moles of ammonia contained in the aqueous ammonia divided by moles of molybdenum contained in the ammonium dimolybdate is selected from about 1.2 to about 2, such as 1.5 to about 1.8.

Step (ii) can include a stoichiometric excess of the hydrogen sulfide. In some embodiments, the tetrathiomolybdate solution in step (ii) or step (iii) is supersaturated.

In some embodiments, the tetrathiomolybdate solution includes no detectable $[MoOS_3]^{2-}$ by UV-Vis. In other embodiments, the tetrathiomolybdate solution further includes a non-zero amount of $[MoOS_3]^{2-}$. For example, the $[MoS_4]^{2-}/[MoOS_3]^{2-}$ ratio in the tetrathiomolybdate solution can be between about 3 and about 1000, such as between about 5 and about 100.

In some embodiments, the Co(II) solution in step (iii) is a cobalt acetate solution, a cobalt sulfate solution, or another Co(II) solution. Mixtures of Co(II) solutions can be employed, if desired.

Step (iv) can be conducted at a pH between about 2 to about 5, such as about 2.5 to about 3.5. In some embodiments, step (iv) is conducted at a pH of about 3.

Step (v) can include filtering in the presence of air, but it is preferable to filter in the presence of a substantially inert environment.

Optionally, this method further includes washing the filter cake after step (v) with water. The amount of water used for washing can vary. In some embodiments, the volume of water used for the washing is less than the volume of the filter cake. In other embodiments, the volume of water used for the washing is at least one volume of the filter cake, or at least two volumes of the filter cake. Preferably, washing removes at least 95%, more preferably at least 99%, of sulfates present prior to the washing.

In some embodiments, the filter cake is not dried between steps (v) and (vi). Step (vi) can be initiated while the filter cake is still moist. In some embodiments, the period of time between steps (v) and (vi) is less than 1 day, while preferably maintaining a substantially inert environment. Preferably, step (vi) is carried out immediately after step (v).

In preferred embodiments, thermal processing in step (vi) includes drying in a substantially inert environment. In preferred embodiments, step (vi) also includes calcining in a substantially inert environment. It is preferable to both dry and calcine in a substantially inert environment.

A single temperature can be employed for thermal processing, but it is preferable to employ multiple temperatures for different stages of thermal processing in step (vi). Thermal processing can be carried out in a single apparatus, or in multiple apparatus.

In some variations of the invention, step (vi) includes drying at a drying temperature and calcining at a calcination temperature which is higher than the drying temperature. The drying temperature can be selected from, for example, about 80-200° C., such as about 100-150° C. The calcination temperature can be selected from about 350-650° C., such as about 450-550° C.

In some embodiments, calcining is conducted for a calcination time selected from about 10 minutes to about 4 hours, such as about 1-2 hours. In some embodiments, the calcined material is then cooled in a substantially inert environment.

In certain embodiments, step (vi) further includes dwelling at an intermediate temperature higher than the drying temperature and lower than the calcination temperature. This intermediate temperature can be selected from about 120-350° C., such as about 200-300° C. The dwell time can be from about 1-24 hours, such as about 2-16 hours, or about 4-8 hours.

The calcined material according to the invention can be combined with a base promoter selected from the alkali or alkaline earth series, thereby producing a base-promoted catalyst. In some embodiments, the base promoter comprises potassium.

In some variations, the base promoter is introduced to the filter cake prior to step (vi). In some embodiments of these variations, the base promoter can be selected from the group consisting of potassium hydroxide, potassium carbonate, potassium oxalate, and potassium acetate. The base promoter can be added in solid form to the filter cake and then collectively subjected to thermal processing.

Base-promoted catalysts can be employed for alcohol synthesis. In some embodiments, syngas is reacted over the base-promoted catalyst (produced by the methods taught herein) to produce at least one $C_1$-$C_4$ alcohol, such as ethanol.

In some embodiments, alcohol synthesis further comprises co-feeding methanol. The methanol can be co-fed in an amount in equilibrium with the syngas, or at less than an amount in equilibrium with the syngas, for example.

Some variations of the present invention provide a method for making a cobalt-molybdenum-sulfide composition, the method comprising the steps of:

(i) dissolving ammonium dimolybdate, $[NH_4]_2[Mo_2O_7]$, in aqueous ammonia, thereby producing a molybdate solution;

(ii) combining hydrogen sulfide with at least some of the molybdate solution, thereby producing a tetrathiomolybdate solution comprising $[MoS_4]^{2-}$;

(iii) combining a Co(II) solution with at least some of the tetrathiomolybdate solution to form a first precipitate within a suspension;

(iv) combining sulfuric acid with at least some of the suspension, to form a second precipitate;

(v) filtering the second precipitate, wherein the filtering removes a portion of water present in the second precipitate, thereby creating a filter cake;

(vi) thermally processing the filter cake to produce a calcined material comprising cobalt, molybdenum, and sulfur;

wherein at least some of the cobalt and some of the sulfur are present as a cobalt-sulfur association, and wherein the molar ratio of sulfur to cobalt (S:Co) in the association is at least 1.2, the molar ratio S:Co calculated after assuming all of the molybdenum is present as $MoS_2$.

The molar ratio S:Co is at least 1.5, such as at least 2.0, in some embodiments.

Some variations of the invention provide a catalyst composition comprising Mo, Co, and S, the composition produced according to a process that includes the steps of:

(i) dissolving ammonium dimolybdate, $[NH_4]_2[Mo_2O_7]$, in aqueous ammonia, thereby producing a molybdate solution;

(ii) combining hydrogen sulfide with at least some of the molybdate solution, thereby producing a tetrathiomolybdate solution comprising $[MoS_4]^{2-}$;

(iii) combining a Co(II) solution with at least some of the tetrathiomolybdate solution to form a first precipitate within a suspension;

(iv) combining sulfuric acid with at least some of the suspension, to form a second precipitate;

(v) filtering the second precipitate, wherein the filtering removes a portion of water present in the second precipitate, thereby creating a filter cake;

(vi) thermally processing the filter cake to produce a calcined material comprising cobalt, molybdenum, and sulfur.

In some embodiments, the catalyst composition includes $MoS_2$ and $CoS_2$ in intimate contact. In some embodiments, at least some of the cobalt and some of the sulfur are present as a cobalt-sulfur association, and wherein the molar ratio of sulfur to cobalt (S:Co) in the association is at least 1.2, preferably at least 1.5, and more preferably at least 2.0. The molar ratio S:Co can be calculated after assuming all of the molybdenum is present as $MoS_2$. The catalyst composition can further include a base promoter selected from the alkali or alkaline earth series, such as potassium.

DETAILED DESCRIPTION OF EMBODIMENTS OF THE INVENTION

Figure 1A:
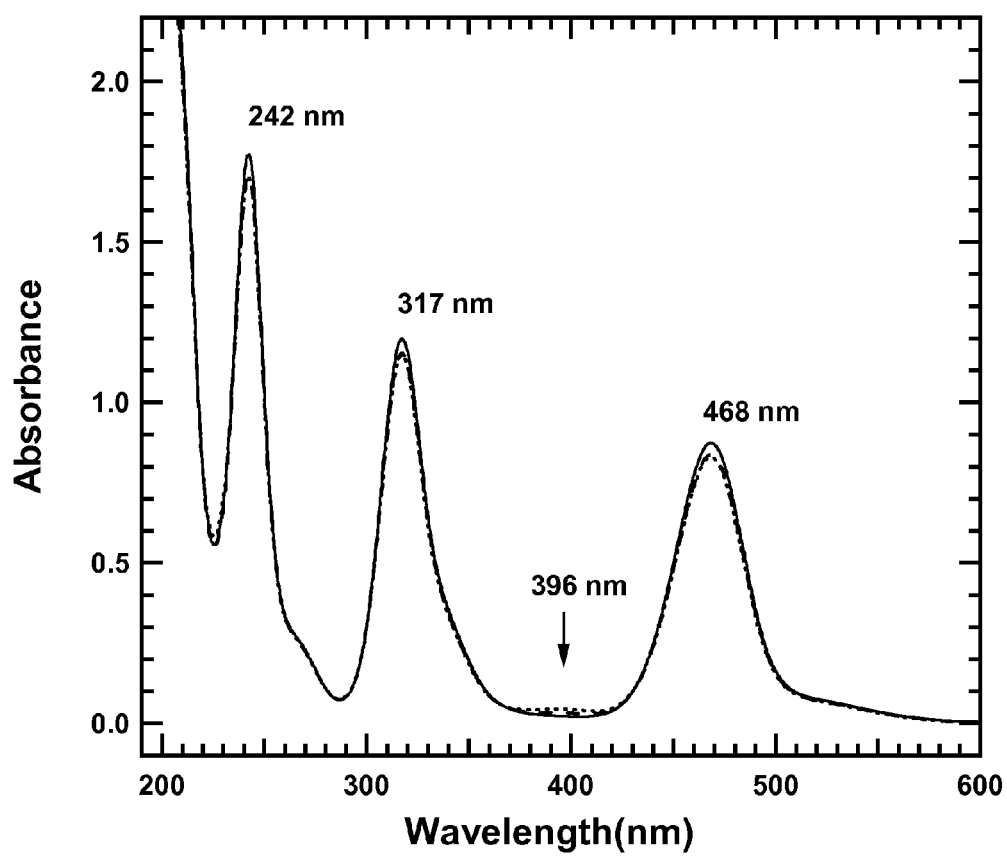
FIG. 1A depicts a UV-Vis spectra scan that illustrates conversion of oxytrithiomolybdate to tetrathiomolybdate species in solution, according to Example 1 of this invention.

This description will enable one skilled in the art to make and use the invention, and it describes several embodiments, adaptations, variations, alternatives, and uses of the invention, including what is presently believed to be the best mode of carrying out the invention.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in its respective testing measurements.

As used herein, "$C_1$-$C_4$ alcohols" means one or more alcohols selected from methanol, ethanol, propanol, and butanol, including all known isomers of such compounds. While preferred embodiments are described in relation to high selectivities to methanol and/or ethanol, the invention can also be practiced in a manner that gives high selectivities to propanol and/or butanol, or certain combinations of selectivities to various alcohols.

The present invention will now be described by reference to the following detailed description and accompanying drawings which characterize and illustrate some preferred embodiments for producing ethanol. This description by no means limits the scope and spirit of the present invention.

In some embodiments, a first step towards synthesis of preferred catalysts is to dissolve ammonium dimolybdate ("ADM") in aqueous ammonia at a pH of about 7.5-11, preferably about 9-9.5 at ambient temperature or a pH of about 7.5-8 at about 60° C., for example. Generally, this step can be conducted from about 10° C. to about 80° C., in various embodiments. ADM, which can be written as $[NH_4]_2[Mo_2O_7]$, has a chain structure with tetrahedral and edge-bridged octahedral molybdenum. ADM is commercially available (e.g., Climax Molybdenum, Iowa, U.S.).

Ammonium molybdate hydrate, $[NH_4]_6[Mo_7O_{24}]\cdot 4H_2O$, contains an edge - and face-fused oxo octahedral with Mo at the center. Since half the molybdenum in solid-state ADM is tetrahedral (sharing a vertex with adjoining octahedral Mo) and the other half of Mo, which is octahedral, merely shares a fused edge (not fused faces) with octahedral Mo, ADM can be considered as "preactivated" for attack by sulfide to make $[MoS_4]^{2-}$. Therefore, solutions at pH of about 9 derived from ADM will contain primarily tetrahedral $[MoO_4]^{2-}$ and $[Mo_2O_7]^{2-}$. These coordinately unsaturated species are prone to repeated nucleophilic attack from sulfide, $HS^-$, or even $H_2S_{aq}$ species. Without being limited by any hypothesis, this attack may occur via 5-coordinate intermediates at Mo, followed by proton transfer or uptake at oxygen and departure of water. Preferably, no intermediate precipitates are observed.

In preferred embodiments of the present invention, when ADM is employed, there is no need for digestion of condensed heptamolybdate clusters to lower-nuclearity Mo clusters or monomers. Omission of this step can result in practical kinetics with respect to dissolution and precipitation (e.g., avoiding intermediate precipitates that do not completely redissolve). The ADM precursor can be a reactive precursor to a number of desired molybdenum-sulfide targets, including $[NH_4]_2MoS_4$ (which can be referred to as "ATTM").

If there is insufficient aqueous ammonia present in solution, the pH can become slightly acidic. In this event, ATTM solubility can decrease. Furthermore, complete deprotonation of the sulfide (to $S^{2-}$) can become difficult at reduced pH. If $HS^-$ and $H_2S$ remain in solution, incomplete conversion of $[MoO_4]^{2-}$ to $[MoS_4]^{2-}$ can result.

Excess amounts of ammonia can also be problematic. It is believed that when excess ammonia is present during the final sulfidation from oxytrithiomolybdate to tetrathiomolybdate, ammonia can compete with the trithiomolybdate dianion $[MoOS_3]^{2-}$ for $H_2S$, thereby producing ammonium hydrosulfide ($NH_4SH$), for example. It has been observed that even in the presence of excess sulfur ($H_2S$), sulfidation of oxytrithiomolybdate does not substantially occur (according to UV-Vis analysis) when too much ammonia is present.

The molar ratio of ammonia to molybdenum is therefore regarded as an important parameter. In some embodiments, the molar ratio of ammonia to molybdenum during this first step is selected from about 1 to about 5, preferably from about 1.2 to about 2, and more preferably from about 1.5 to about 1.8, such as 1.6-1.7.

In some embodiments, a second step towards synthesis of preferred catalysts is to add hydrogen sulfide ($H_2S$) to the molybdate solution produced in the first step, thereby producing ATTM. The predominance of coordinatively unsaturated, tetrahedral $[MoO_4]^{2-}$ can activate these solutions for reaction with $H_2S$ to yield $[MoS_4]^{2-}$. The ATTM solution can include an ATTM concentration that is lower than saturation, or about at saturation. In some embodiments, the ATTM solution is slightly supersaturated. The heat provided by reaction exothermicity can be beneficial. For example, such heat can assist later filtration, especially after the pH drops.

The final sulfidation from oxytrithiomolybdate to tetrathiomolybdate is known to be kinetically slow. Excess $H_2S$ can be employed to drive the sulfidation to completion, when ammonia is not present in excess. Due to safety considerations, however, excess $H_2S$ can be undesirable if it does not all convert in the reaction. Preferably, if an excess of $H_2S$ is introduced, sufficient time should be allowed for the $H_2S$ to react. Such time can be, for example, at least about 15 minutes, and preferably at least about 30 minutes (see Example 1 and FIGS. 1A and 1B).

Excessive waiting times (e.g., greater than about 1 hour) are not desired, though, as atmospheric oxygen can eventually react with the mixture. Also, the reaction mixture is typically in an excess of water. Excess waiting times can promote hydrolysis, which will convert the molybdenum species back to the oxythiomolybdates. The molybdate species can even undergo complete hydrolysis, evolving $H_2S$ in the process.

In some embodiments, tetrathiomolybdate solutions include no detectable $[MoOS_3]^{2-}$ by UV-Vis (see e.g. Example 1). In other embodiments, the conversion of $[MoO_4]^{2-}$ to $[MoS_4]^{2-}$ is not quantitative, so that there remains a non-zero amount of $[MoOS_3]^{2-}$ (oxytrithiomolybdate dianion) in solution. In this case, the ratio $[MoS_4]^{2-}/[MoOS_3]^{2-}$ will be less than infinity, such as less than $10^4$, $10^3$, $10^2$, or 10. This ratio should be greater than zero for preferred intermediate materials. An exemplary range of $[MoS_4]^{2-}/[MoOS_3]^{2-}$ is about 3-1000, such as about 5-100.

A reaction vessel with high aspect ratio can be used. $H_2S$ can be added into the bottom of this reaction vessel. One role of the high aspect ratio is to require the hydrogen sulfide to travel a substantial distance through the solution before it can break through to the surface, thereby increasing the efficiency of $H_2S$ consumption. In preferred embodiments, the reaction vessel includes an agitator suitable for high shear rates and radial flow. It is beneficial to create small bubbles of $H_2S$, so that mass-transfer resistance from the gas phase to the liquid phase is reduced. Also, it is beneficial to create at least some radial flow, rather than substantially axial flow, to increase the residence time and conversion of $H_2S$.

A person skilled in the art will appreciate that a variety of apparatus can be employed to achieve the desired function. For example, the reaction vessel can employ helical agitators, rotor-stator mixers, or other types of mixing devices. A preferred agitator is a dispersion agitator blade. The reaction vessel can also include one or more baffles, in some embodiments, to increase mass transfer. Additionally, $H_2S$ bubble size can be reduced through the use of microbubble generators, high-velocity gas spargers, and the like.

Addition of $H_2S$ can be advantageous compared to that of $[NH_4]_2S$. One advantage of $H_2S$ over $[NH_4]_2S$ is that, in some embodiments, lower volumes of water are used and very little added ammonia is used. This decreases the volumes of liquor to be filtered, which will tend toward improved operational efficiency. This can also decrease the stress on wastewater-handling systems. Further, when $H_2S$ is employed, less ammonia is evolved during calcination and, consequently, less ammonia needs to be scrubbed from calciner effluent.

It is noted that reference to $[NH_4]_2S$ is a formalism for the purpose of the present invention. Solutions can contain large quantities of the $HS^-$ anion—that is, $[NH_4][HS]$ salt and free ammonia. There can also be significant quantities of free hydrogen sulfide in solution, depending on the solution equilibrium as a function of pH and temperature.

Addition of $H_2S$ and subsequent precipitations can be carried out at or near ambient temperature, such as about 15-25° C. In other embodiments, these steps can be carried out at elevated temperatures, such as 25-75° C., for example. The temperature can also vary during the course of $H_2S$ and addition and subsequent precipitations. Some of the precipitation chemistry is exothermic, so moderate temperature rises can take place.

In some embodiments, a third step towards synthesis of preferred catalysts is to add Co(II) acetate solution to the ATTM solution, thereby causing a first precipitate to quickly form. This first precipitate may contain $CoMoS_4$, $[NH_4]_2[Mo_2CoS_8]$, CoS, and/or other compounds as can be determined by ordinary analysis. This precipitation can alter the composition of the remaining liquor. The resulting suspension contains both a precipitate as well as dissolved species. It will be recognized by a skilled artisan that other salts of cobalt can be employed for this step, such as (but not limited to) cobalt sulfate.

This first precipitate can be richer in cobalt compared to the overall reaction mixture. Without being limited by a theory, this precipitate may be caused by excess $HS^-$ and $H_2S$ in solution; this precipitate may be the origin of a crystalline $CoS_2$ phase that can be observed by XRD analysis of certain preferred catalyst compositions. This crystalline $CoS_2$ phase may not be catalytically active per se, but it may provide a catalyst support and/or sulfur source for highly-dispersed $MoS_2$ crystallites.

In some embodiments, a fourth step towards synthesis of preferred catalysts is to add this suspension, from the third step above, to another reaction vessel together with simultaneous addition of (preferably concentrated) sulfuric acid. It is important to stir or agitate the mixture, for safety reasons. An additional precipitation reaction occurs to produce a second precipitate which preferably contains substantially all of the first precipitate. The precipitation is preferably conducted at a pH in the 2-5 range, more preferably about 3-3.5. Another role of the sulfuric acid (or another acid) can be that precipitation of ATTM under moderately acidic conditions results in a large particle-size precipitate that is easier to filter. Moderate acidity promotes grain growth of the precipitate. In certain embodiments, a final pH of about 3 results in a coarser precipitate that is easier to filter using manufacturing equipment known in the art.

Suitable filtering apparatus that can be employed include, but are not limited to, rotary vacuum filters, high-pressure gas filters (such as PneumaPress® filters), cartridge filters, membrane filters, and so on, as is known to a skilled artisan. Some variations utilize combinations of filters and/or introduce other separation functions, such as centrifuging.

Reaction of $[NH_4]_2[MoS_4]$ with sulfuric acid can result, according to Wang et al., in $MoS_3$ ("Synthesis of molybdenum disulphide by acidification of ammonium tetrathiomolybdate solutions," *Mater. Sci. Lett.*, vol. 6, 494-496, 1996). $MoS_3$ is an amorphous compound, according to Chang and Chan, "Infrared and Raman studies of amorphous $MoS_3$ and poorly crystalline $MoS_2$," *J. Catal.*, vol. 72, 139-148, 1981, containing both $S^{2-}$ and $S_2^{2-}$ species and can be formulated as $Mo(S)(S_2)$.

In some embodiments, a fifth step towards synthesis of preferred catalysts is to filter the suspension produced in the fourth step above. It is preferred to quickly remove the precipitate from the mother liquor, to avoid leaching of metals which can occur due to the low pH of the mother liquor. The precipitate can be filtered in air, or in some other environment, such as a substantially inert environment. Preferably, the cake should not go completely dry before the sixth step below, as a dry cake can be unstable and pyrophoric. Excess water retained in the filter cake, after washing and filtration but prior to thermal processing (described below), aids in avoiding gross oxidation of the precipitate by acting as a barrier between oxygen and the precipitate. Wet cakes can therefore provide a handling convenience.

The cake can be washed with water and/or some other solvent. The amount of water to be used for washing can vary, such as less than one volume of wet cake, about 1-2 volumes of wet cake, or more than 2 cake volumes. In some embodiments, washing is conducted until sulfate ($SO_4^{2-}$) concentration drops below a predetermined level or until a certain fraction of sulfate is removed, such as 90%, 95%, or 99%. It is desired to substantially wash out sulfates (such as ammonium sulfate) from the filter cake, to avoid later formation of potassium sulfate after introducing potassium (a promoter for alcohol synthesis). Potassium sulfate, $K_2SO_4$, is known to be a poor promoter of alcohol synthesis.

"Substantially inert" means that an environment includes a sufficient quantity or concentration of inert gases (e.g., $N_2$, Ar, He, $CO_2$, and the like) such that reactive gases (e.g., $O_2$), if present, do not tend to cause measurable side reactions. Of course, "substantially inert" can mean completely inert in some embodiments; however, it is recognized that there will almost always be at least one molecule of a reactive gas present in a substantially inert environment.

In preferred embodiments, a sixth step towards synthesis of preferred catalysts is to subject the wet cake from the fifth step to thermal processing. As used herein, "thermal processing" includes drying and calcining During thermal processing, volatile species comprising water, sulfur, ammonia, and hydrogen sulfide are removed. It will be recognized that these volatile species may not be completely removed, even if thermodynamics would predict perfect removal at equilibrium.

Drying and calcining of the wet filter cake can be performed in a single, continuous step, in some embodiments. In preferred variations, drying and calcining are both conducted in a substantially inert atmosphere, thereby preventing intermediate exposure to oxygen. Such inert drying/calcining has been found experimentally to produce improved catalysts for $C_1$-$C_4$ alcohol production from syngas. Calcining should be conducted in a substantially inert atmosphere to avoid damage to the material.

Additionally, it is preferred to dry and calcine the filter cake with minimal storage of the filter cake. Minimal storage means less than 1 week, preferably less than 2 days, more preferably less than 1 day, and most preferably substantially immediately after filtration.

The thermal processing can be conducted under flowing nitrogen or another inert gas. A variety of temperatures and times can be employed for thermal processing. Temperatures generally refer to average applied temperatures (typically by external heating) within a vessel or container that contains the material being processed. The surface and/or bulk temperature of the material itself can, of course, be different than the applied temperature.

In some embodiments, a first temperature is associated with drying, i.e., water removal. The drying temperature can be selected, for example, from about 80-150° C., such as about 120° C. It is typical for the temperature of the material to increase as water is driven off and more heat can go to heat up the solid material rather than toward the heat of vaporization of water.

Optionally, the temperature is raised to a second, intermediate temperature and the material held there for a period of time ("dwell time"). The material is preferably dried prior to this dwell time, although that is not necessary. The intermediate temperature can be selected, for example, from about 100-400° C., such as about 200-300° C., e.g. about 250° C. The dwell time at this intermediate temperature can vary. For example, the dwell time can selected from about 1-24 hours or more, such as 4, 8, 12, or 16 hours, which times are exemplary only. The dwell time can elapse overnight (e.g., about 12-18 hr), which can be resource-efficient. With reference to Example 2 herein, it is preferred to employ relatively short dwell times, such as 8 hours or less, in conjunction with relatively high intermediate temperatures, such as 250° C. or higher.

After drying and optional dwelling, the material is calcined. The calcination temperature can be selected from about 350-650° C., such as about 450-550° C., e.g. about 500° C. (see also Example 2). The calcination time can be, for example, less than 1 hour, about 1 hour, about 2 hours, or more, with care being taken to not cause thermal damage such as sintering. The calcining process should take place at temperatures below the effective melting points of the materials contained in the filter cake. Excessive calcination conditions can also promote non-preferred crystallization of some species present in the precipitate. Calcination can be conducted in any suitable apparatus, such as (for example) a rotary retort in a furnace. Calcination can be carried out in the same apparatus as that used for drying, or in a different apparatus.

Alternatively, a single temperature can be selected for thermal processing. This temperature can be selected from, for example, about 200-600° C. It will be recognized that even with a constant temperature associated with a heat source (e.g., a furnace), there can be variations in surface and/or internal temperatures of the material as it undergoes water removal and various structural changes that can be exothermic or endothermic. Also, there will always be a time associated with heating up the material to a calcination temperature, and drying can certainly occur during this heat-up phase.

After calcination, it is preferred to cool down the calcined material under an inert gas such as $N_2$. Unloading the calcined material is preferably performed in a substantially inert atmosphere, in some embodiments.

It is presently believed that the aforementioned synthesis steps can generate a catalyst precursor with a high sulfur/metals ratio, such composition being preferred for production of ethanol and other alcohols. In some methods according to the six steps recited herein, the final composition comprises an intimate mixture of two moles of $MoS_2$ per one mole of $CoS_2$.

More generally, the methods of the present invention are suitable for synthesizing catalyst compositions for catalyzing the conversion of syngas into products comprising at least one $C_1$-$C_4$ alcohol, the catalyst composition comprising cobalt, molybdenum, and sulfur, wherein at least some of the cobalt and some of the sulfur are present as a cobalt-sulfur association, and wherein the molar ratio of sulfur to cobalt (S:Co) in the association is at least 1.2. This molar ratio S:Co can be calculated after assigning some of the sulfur to molybdenum by assuming all molybdenum is present in the composition as $MoS_2$, optionally after subtracting any elemental sulfur present. S:Co can also be calculated after subtracting any sulfur that is soluble in 3 N HCl, if desired. In some embodiments, the molar ratio S:Co is at least 1.5, at least 2.0, or between about 2.0 and about 4.0.

The compositions that can be produced by the present methods include at least some catalyst compositions described and/or claimed in co-pending U.S. patent application Ser. No. 12/204,543, filed Sep. 4, 2008 or U.S. patent application Ser. No. 12/769,850, filed Apr. 29, 2010, which patent applications are hereby fully incorporated by reference herein for all purposes.

In another aspect of the invention, the catalyst compositions are used in reactors for the production of $C_1$-$C_4$ alcohols. It is preferable that the catalyst compositions be modified to include a "base promoter" of an alkali or alkaline earth series metal, such as potassium, in free or combined form. Such base promoters characteristically increase selectivities to alcohols that are larger than methanol. In some embodiments, at least one base promoter is selected from the group consisting of barium, strontium, scandium, and yttrium. In some embodiments, at least one base promoter is selected from the lanthanide-series metals. The base promoter can be introduced by any known means, such as by grinding in dry form.

In certain variations of this invention, one or more base promoters are introduced to the wet cake prior to drying and calcination. For example, after the fifth step recited above but before the sixth step, the wet cake can be mixed with solid potassium hydroxide in the form of pellets, powder, or some other geometry. The combined material can then be thermally processed in accordance with the present invention. It has been observed that promoted catalysts produced by this procedure can have similar activity and selectivity (to alcohols), compared to catalysts produced by dry mixing, for example.

Methanol, ethanol, or both methanol and ethanol can be desired alcohol products. In some variations wherein ethanol is a desired product, methanol co-feed can be utilized to increase selectivities and yields toward ethanol. The co-fed methanol can be fresh or recycled methanol. These embodiments are premised on the realization that, for certain catalyst compositions obtained in accordance with this invention, ethanol yields increase with the approach to methanol/syngas equilibrium. By co-feeding methanol, the reactor can be operated at a lower temperature to achieve the same or better ethanol yield. A lower temperature tends to suppress direct hydrocarbon synthesis as well as reduction of alcohols to hydrocarbons, thereby enhancing selectivity to ethanol. In some embodiments, the amount of methanol co-fed can be about an amount in equilibrium with the syngas fed, or less, such as about 25-75% of the equilibrium amount.

The catalyst can take the form of a powder, pellets, granules, beads, extrudates, and so on. When a catalyst support is optionally employed, the support may assume any physical form such as pellets, spheres, monolithic channels, etc. The supports may be coprecipitated with active metal species; or the support may be treated with the catalytic metal species and then used as is or formed into the aforementioned shapes; or the support may be formed into the aforementioned shapes and then treated with the catalytic species.

In embodiments of the invention that employ a catalyst support, the support is preferably (but not necessarily) a carbon-rich material with large mesopore volume, and further is preferably highly attrition-resistant. One carbon support that can be utilized is "Sibunit" activated carbon (Boreskov Inst. of Catalysis, Novosibirsk, Russia) which has high surface area as well as chemical inertness both in acidic and basic media (Simakova et al., Proceedings of SPIE—Volume 5924, 592413, 2005). An example of Sibunit carbon as a catalyst support can be found in U.S. Pat. No. 6,617,464 (Manzer).

It is preferable to maintain a starting catalyst under inert conditions prior to loading and activating the starting catalyst. It will be recognized that, practically, it can be difficult to completely prevent any air exposure. In preferred embodiments, less than 6 hours, more preferably less than 3 hours, and most preferably less than 1 hour air exposure occurs with the starting catalyst.

In some embodiments, conditions effective for producing alcohols from syngas include a feed hydrogen/carbon monoxide molar ratio ($H_2/CO$) from about 0.2-4.0, preferably about 0.5-2.0, and more preferably about 0.5-1.5. These ratios are indicative of certain embodiments and are not limiting. It is possible to operate at feed $H_2/CO$ ratios less than 0.2 as well as greater than 4, including 5, 10, or even higher. It is well-known that high $H_2/CO$ ratios can be obtained with extensive steam reforming and/or water-gas shift in operations prior to the syngas-to-alcohol reactor.

In embodiments wherein $H_2/CO$ ratios close to 1:1 are desired for alcohol synthesis, partial oxidation of the carbonaceous feedstock can be utilized. In the absence of other reactions, partial oxidation tends to produce $H_2/CO$ ratios close to unity, depending on the stoichiometry of the feedstock.

When, as in certain embodiments, relatively low $H_2/CO$ ratios are desired, the reverse water-gas shift reaction ($H_2 + CO_2 \rightarrow H_2O + CO$) can potentially be utilized to consume hydrogen and thus lower $H_2/CO$. In some embodiments, $CO_2$ produced during alcohol synthesis or elsewhere, can be recycled to the reformer to decrease the $H_2/CO$ ratio entering the alcohol-synthesis reactor. Other chemistry and separation approaches can be taken to adjust the $H_2/CO$ ratios prior to converting syngas to alcohols, as will be appreciated. For example, certain commercial membrane systems are known to be capable of selectively separating $H_2$ from syngas, thereby lowering the $H_2/CO$ ratio.

In some embodiments, conditions effective for producing alcohols from syngas include reactor temperatures from about 200-400° C., preferably about 250-350° C.; and reactor pressures from about 20-500 atm, preferably about 50-200 atm or higher. Generally, productivity increases with increasing reactor pressure. Temperatures and pressures outside of these ranges can be employed.

In some embodiments, conditions effective for producing alcohols from syngas include average reactor residence times from about 0.1-10 seconds, preferably about 0.5-2 seconds. "Average reactor residence time" is the mean of the residence-time distribution of the reactor contents under actual operating conditions. Catalyst space times or catalyst contact times can also be calculated by a skilled artisan and these times will typically also be in the range of 0.1-10 seconds, although it will be appreciated that it is certainly possible to operate at shorter or longer times.

In general, the specific selection of catalyst configuration (geometry), $H_2/CO$ ratio, temperature, pressure, residence time (or feed rate), and other reactor-engineering parameters will be selected to provide an economical process. These parameters are not regarded as critical to the present invention. It is within the ordinary skill in the art to experiment with different reactor conditions to optimize selectivity to a particular product or some other parameter.

Product selectivities can be calculated on a carbon-atom basis. "Carbon-atom selectivity" means the ratio of the moles of a specific product to the total moles of all products, scaled by the number of carbon atoms in the species. This definition accounts for the mole-number change due to reaction. The selectivity $S_j$ to general product species $C_{x_j}H_{y_j}O_{z_j}$ is $$S_j = \frac{x_j F_j}{\sum_i x_i F_i}$$

wherein $F_j$ is the molar flow rate of species j which contains $x_j$ carbon atoms. The summation is over all carbon-containing species ($C_{x_i}H_{y_i}O_{z_i}$) produced in the reaction. In some embodiments, wherein all products are identified and measured, the individual selectivities sum to unity (plus or minus analytical error). In other embodiments, wherein one or more products are not identified in the exit stream, the selectivities can be calculated based on what products are in fact identified, or instead based on the conversion of CO.

In various embodiments of the present invention, the product stream from the reactor may be characterized by reaction selectivities of about 10-60% or higher to methanol and about 10-50% or higher to ethanol. The product stream from the reactor may include up to, for example, about 25% reaction selectivity to $C_{3+}$ alcohols, and up to about 10% to other non-alcohol oxygenates such as aldehydes, esters, carboxylic acids, and ketones. These other oxygenates can include, for example, acetone, 2-butanone, methyl acetate, ethyl acetate, methyl formate, ethyl formate, acetic acid, propanoic acid, and butyric acid.

EXAMPLE 1

This Example 1 demonstrates UV-Vis detection of exemplary conversion of oxytrithiomolybdate to tetrathiomolybdate species in solution.

Figure 1B:
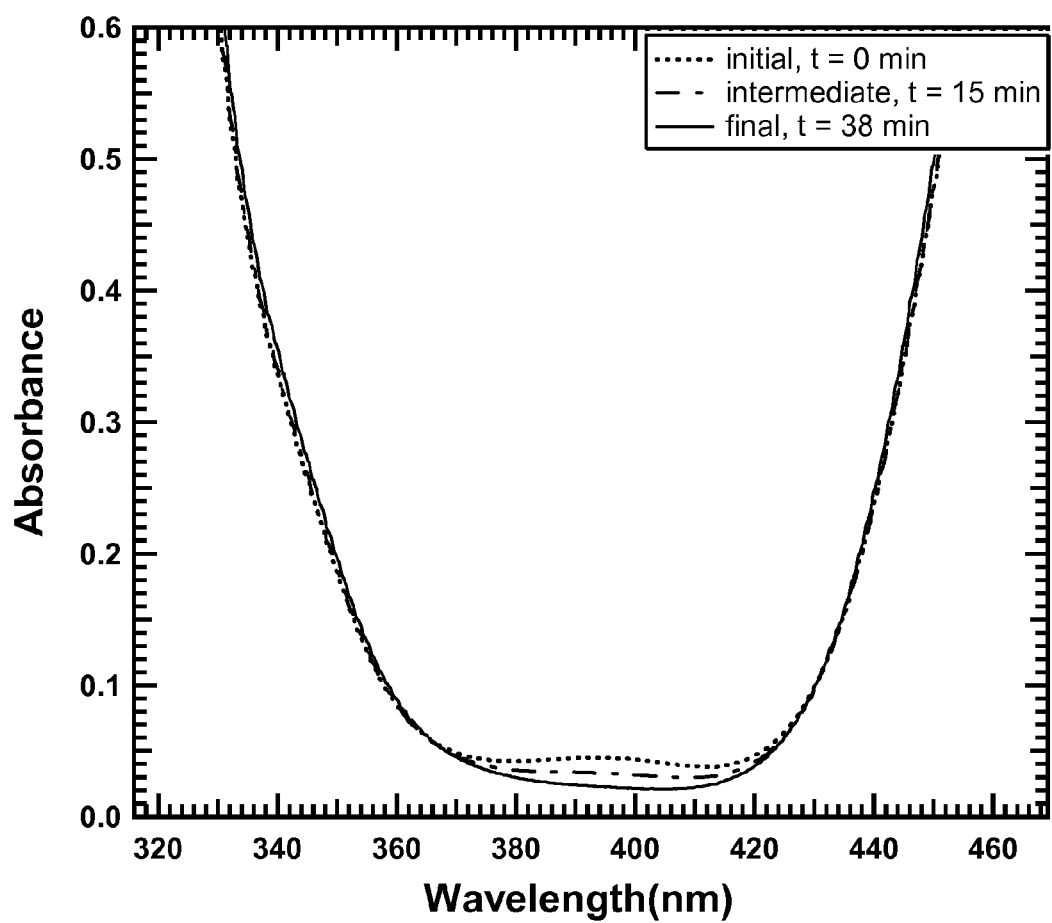
FIG. 1B shows a region of interest on the scan from FIG. 1A.

FIG. 1A depicts a UV-Vis spectra scan from about 200-600 nm in radiation wavelength. FIG. 1B highlights the wavelengths of particular interest from FIG. 1A, namely 320-470 nm. FIG. 1B shows the disappearance of oxytrithiomolybdate species in solution over a period of 38 minutes, suggesting complete or nearly complete conversion of oxytrithiomolybdate to tetrathiomolybdate in this time period.

In addition to the absence of a peak at about 396 nm, FIG. 1A shows three absorbance bands related to ATTM at about 468 nm, about 317 nm, and about 242 nm (±1.5 nm for each transition, per instrument resolution).

EXAMPLE 2

This Example 2 describes the application of Design of Experiments methodology to statistically evaluate experimental effects associated with drying and calcination of cobalt-molybdenum-sulfide precipitates to form precursor powders.

The study includes drying dwell times of 8 and 16 hours, along with drying temperatures of 120° C., 185° C., and 250° C. in a full factorial. After drying, calcination is conducted at about 500° C. for about 1 hour to generate a precursor powder which is then promoted with potassium to form a finished Co/Mo/S/K catalyst powder. Experimental responses are then generated by testing this finished Co/Mo/S/K catalyst in a test reactor at 310° C., 1270 psig, about 3900 GHSV, and $H_2/CO=1.6$ including 7% $CH_4$ and 7% $CO_2$ in the feed.

The experimental results suggest that higher drying temperatures and low dwell times are generally favorable. Decreasing the production of hydrocarbons (such as methane) can be achieved by drying at a temperature lower than about 130° C., or minimizing the dwell time if the drying temperature is greater than 130° C.

Figure 2:
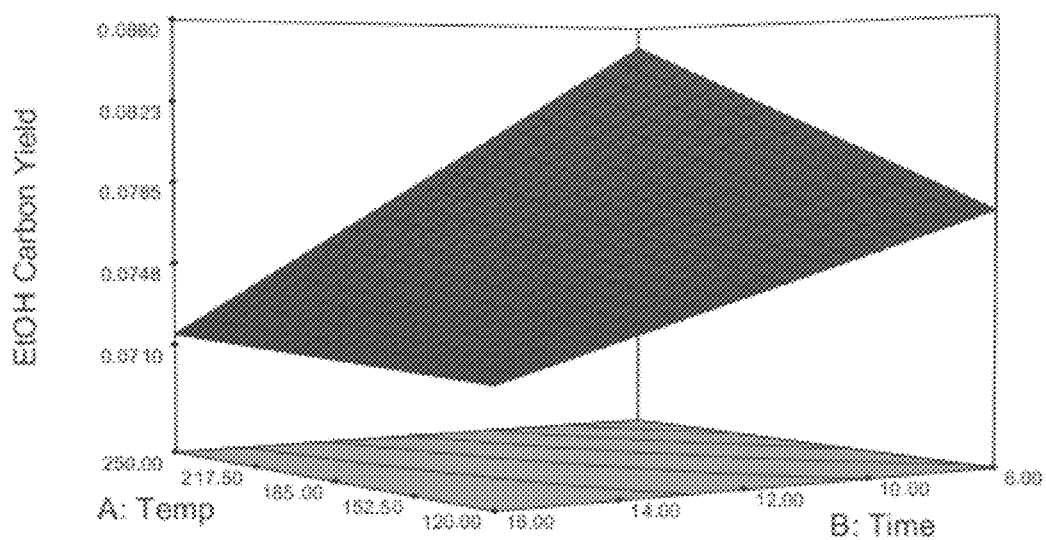
FIG. 2 shows ethanol yield as a function of temperature and time, according to Example 2 of this invention.

Ethanol and methanol production can be favored by maximizing the drying temperature and minimizing the dwell time. Within the constraints of this study, drying at 250° C. for 8 hours is preferable. FIG. 2 shows the ethanol yield response as a function of temperature and time, where the response surface is constructed from experimental data in this example. The results also suggest that drying at even higher temperatures than 250° C. and/or even lower dwell times than 8 hours could be desirable, for $C_1$-$C_2$ alcohol formation.

Figure 3:
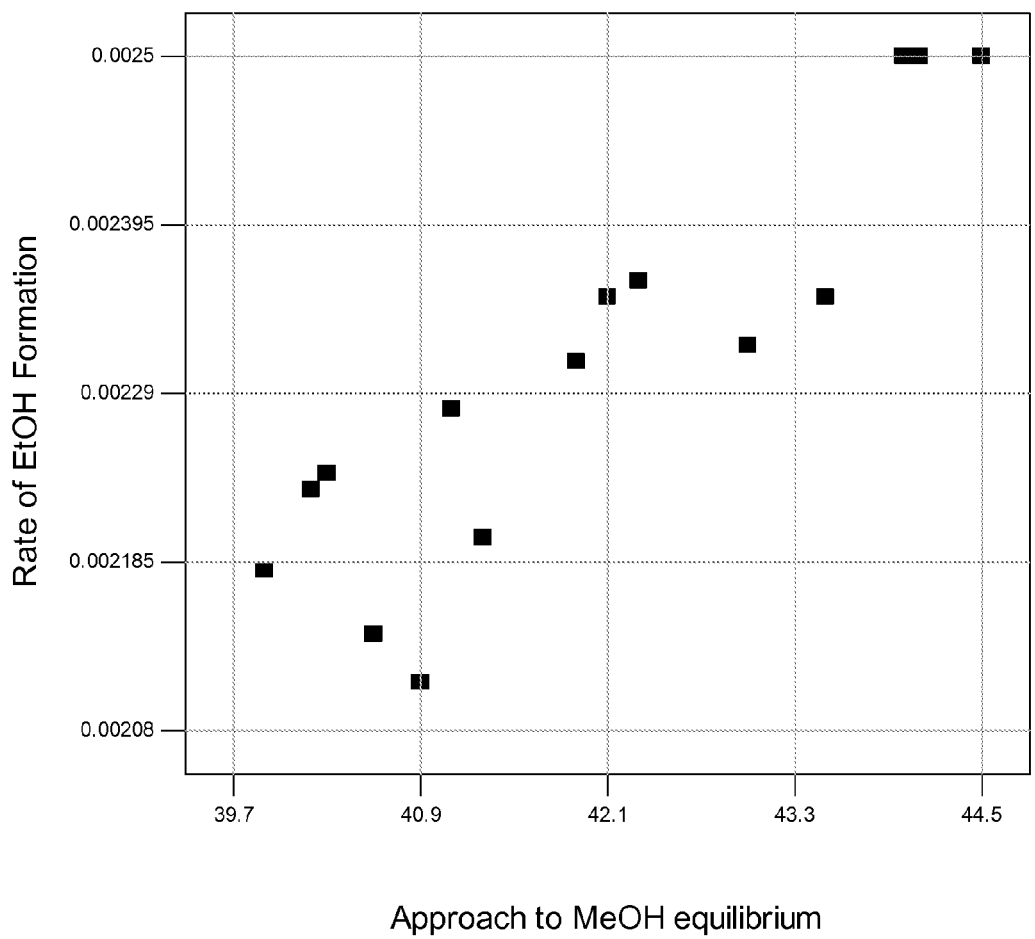
FIG. 3 displays the rate of ethanol formation as a function of the approach to methanol equilibrium, according to Example 2 herein.

FIG. 3 demonstrates that, in this example, the rate of ethanol formation (in moles ethanol per hour per gram of Co/Mo/S) correlates very well with the approach to methanol equilibrium as a percentage of the predicted equilibrium at the relevant conditions.

EXAMPLE 3

In this Example 3, certain variations of the present invention are carried out, for illustration.

In step 1, ammonium dimolybdate, $[NH_4]_2[Mo_2O_7]$, is dissolved in ammoniacal water. Ammonia is present in 15% excess of the stoichiometric reaction:

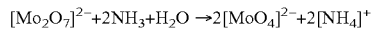

$$[Mo_2O_7]^{2-}+2NH_3+H_2O \rightarrow 2[MoO_4]^{2-}+2[NH_4]^+$$

The molybdenum concentration is 0.3 molar.

In step 2, ammonium molybdate is converted to ammonium tetrathiomolybdate by reaction with H2S, utilizing about 4.2±0.1 moles $H_2S$/mol Mo.

In step 3, a solution of cobalt acetate tetrahydrate is prepared, at about the solubility limit (approximately a 1 M solution).

In step 4, the cobalt acetate is added to the tetrathiomolybdate solution. An initial precipitate forms, but some thiomolybdate remains in solution. The result is a Co—Mo—S suspension.

In step 5, the precipitation is finished by pumping the Co—Mo—S suspension into a precipitation vessel. The vessel is initially charged with 2% v/v sulfuric acid solution. The volume of this initial charge is about 8% of the total amount of liquid to be filtered. Concentrated sulfuric acid is added simultaneously with the Co—Mo—S suspension to the precipitation vessel. Hydrogen sulfide evolves during this acid precipitation. Throughout the precipitation, the pH is maintained in the range 2.5-3.0.

In step 6, the precipitate is filtered and washed, yielding about 2 kg of material. Washing is performed by washing once with two liters of DI water prior to calcination.

In step 7, the wet cake is dried and then subsequently calcined at about 500° C. for about 1 hour, all under $N_2$.

In step 8, calcined material is packed under $N_2$ for further processing into finished catalyst.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A method for making a cobalt-molybdenum-sulfide composition, said method comprising the steps of:
   (i) dissolving ammonium dimolybdate, $[NH_4]_2[Mo_2O_7]$, in aqueous ammonia, thereby producing a molybdate solution;
   (ii) combining hydrogen sulfide with at least some of said molybdate solution, thereby producing a tetrathiomolybdate solution comprising $[MoS_4]^{2-}$;
   (iii) combining a Co(II) solution with at least some of said tetrathiomolybdate solution to form a first precipitate within a suspension;
   (iv) combining sulfuric acid with at least some of said suspension, to form a second precipitate;
   (v) filtering said second precipitate, wherein said filtering removes a portion of water present in said second precipitate, thereby creating a filter cake; and
   (vi) thermally processing said filter cake to produce a calcined material comprising cobalt, molybdenum, and sulfur,
   wherein step (vi) includes drying said filter cake in a substantially inert environment to produce a dried material and calcining said dried material to produce said calcined material.

2. The method of claim 1, wherein in step (i), the ratio of moles of ammonia contained in said aqueous ammonia divided by moles of molybdenum contained in said ammonium dimolybdate is selected from about 1.2 to about 2.

3. The method of claim 2, wherein said ratio is selected from about 1.5 to about 1.8.

4. The method of claim 1, wherein step (ii) includes a stoichiometric excess of said hydrogen sulfide to produce said $[MoS_4]^{2-}$.

5. The method of claim 1, wherein said tetrathiomolybdate solution in step (ii) or step (iii) is supersaturated.

6. The method of claim 1, wherein said tetrathiomolybdate solution further includes a non-zero amount of $[MoOS_3]^{2-}$.

7. The method of claim 6, wherein the $[MoS_4]^{2-}/[MoOS_3]^{2-}$ ratio in said tetrathiomolybdate solution is between about 5 and about 100.

8. The method of claim 1, wherein said Co(II) solution in step (iii) is a cobalt acetate solution.

9. The method of claim 1, wherein said Co(II) solution in step (iii) is a cobalt sulfate solution.

10. The method of claim 1, wherein step (v) includes filtering in the presence of air.

11. The method of claim 1, wherein step (v) includes filtering in the presence of a substantially inert environment.

12. The method of claim 1, further comprising washing said filter cake after step (v) with water.

13. The method of claim 12, wherein said washing removes at least 99% of sulfates present prior to said washing.

14. The method of claim 1, wherein said filter cake is not dried between steps (v) and (vi).

15. The method of claim 1, wherein step (vi) includes calcining said dried material in a substantially inert environment.

16. The method of claim 1, further comprising cooling said calcined material in a substantially inert environment.

17. The method of claim 1, wherein step (vi) is carried out immediately after step (v).

18. The method of claim 1, further comprising combining said calcined material with a base promoter selected from the alkali or alkaline earth series, thereby producing a base-promoted catalyst.

19. The method of claim 18, wherein said base promoter is selected from the group consisting of potassium hydroxide, potassium carbonate, potassium oxalate, and potassium acetate.

20. The method of claim 18, wherein said base promoter is introduced to said filter cake prior to step (vi).

21. The method of claim 20, wherein said base promoter is added in solid form to said filter cake and then said filter cake with said base promoter are collectively subjected to step (vi).

22. A method for making a cobalt-molybdenum-sulfide composition, said method comprising the steps of:
   (i) dissolving ammonium dimolybdate, $[NH_4]_2[Mo_2O_7]$, in aqueous ammonia, thereby producing a molybdate solution;
   (ii) combining hydrogen sulfide with at least some of said molybdate solution, thereby producing a tetrathiomolybdate solution comprising $[MoS_4]^{2-}$;
   (iii) combining a Co(II) solution with at least some of said tetrathiomolybdate solution to form a first precipitate within a suspension;
   (iv) combining sulfuric acid with at least some of said suspension, to form a second precipitate;
   (v) filtering said second precipitate, wherein said filtering removes a portion of water present in said second precipitate, thereby creating a filter cake; and
   (vi) thermally processing said filter cake to produce a calcined material comprising cobalt, molybdenum, and sulfur,
   wherein step (vi) includes drying at a drying temperature selected from about 80-200° C. and calcining at a calcination temperature selected from about 350-650° C.

23. The method of claim 22, wherein said drying temperature is selected from about 100-150° C.

24. The method of claim 22, wherein said calcination temperature is selected from about 450-550° C.

25. The method of claim 22, wherein said calcining is conducted for a calcination time selected from about 10 minutes to about 4 hours.

26. The method of claim 25, wherein said calcination time is selected from about 1 to 2 hours.

27. The method of claim 22, wherein said drying and calcining are carried out in the same apparatus.

28. The method of claim 22, wherein step (vi) further includes dwelling at an intermediate temperature higher than said drying temperature and lower than said calcination temperature, wherein said dwelling is conducted for a dwell time from about 1-24 hours.

29. The method of claim 28, wherein said intermediate temperature is selected from about 120-350° C.

30. The method of claim 29, wherein said intermediate temperature is selected from about 200-300° C.

31. The method of claim 28, wherein said dwell time is selected from about 2-16 hours.

32. The method of claim 31, wherein said dwell time is selected from about 4-8 hours.

33. A method of producing at least one $C_1$-$C_4$ alcohol, said method comprising:
   (i) dissolving ammonium dimolybdate, $[NH_4]_2[Mo_2O_7]$, in aqueous ammonia, thereby producing a molybdate solution;
   (ii) combining hydrogen sulfide with at least some of said molybdate solution, thereby producing a tetrathiomolybdate solution comprising $[MoS_4]^{2-}$;
   (iii) combining a Co(II) solution with at least some of said tetrathiomolybdate solution to form a first precipitate within a suspension;
   (iv) combining sulfuric acid with at least some of said suspension, to form a second precipitate;
   (v) filtering said second precipitate, wherein said filtering removes a portion of water present in said second precipitate, thereby creating a filter cake;
   (vi) thermally processing said filter cake to produce a calcined material comprising cobalt, molybdenum, and sulfur;
   (vii) combining said calcined material with a base promoter selected from the alkali or alkaline earth series, thereby producing a base-promoted catalyst; and
   (viii) reacting syngas over said base-promoted catalyst to produce at least one $C_1$-$C_4$ alcohol.

34. The method of claim 33, wherein said at least one $C_1$-$C_4$ alcohol is ethanol.

35. The method of claim 33, further comprising co-feeding methanol in an amount in equilibrium with said syngas.

36. The method of claim 33, further comprising co-feeding methanol at less than an amount in equilibrium with said syngas.

37. The method of claim 33, wherein step (vi) includes drying said filter cake in a substantially inert environment to produce a dried material, and then calcining said dried material to produce said calcined material.

38. The method of claim 33, wherein step (vi) includes drying at a drying temperature selected from about 80-200° C. and calcining at a calcination temperature selected from about 350-650° C.

* * * * *